US00PP10361P

United States Patent [19]

Kristiansen

[11] Patent Number: Plant 10,361

[45] Date of Patent: Apr. 28, 1998

[54] ASTER PLANT NAMED 'THYRA VIKING'

[75] Inventor: Kell Kristiansen, Årslev, Denmark

[73] Assignee: Åster Klubben, Arslev, Denmark

[21] Appl. No.: 773,230

[22] Filed: Dec. 23, 1996

[51] Int. Cl.[6] ..... A01H 5/00

[52] U.S. Cl. ..... Plt./68.1

[58] Field of Search ..... Plt./68.1

*Primary Examiner*—James R. Feyrer
*Assistant Examiner*—Elizabeth C. Kemmerer
*Attorney, Agent, or Firm*—C. A. Whealy

[57] ABSTRACT

A distinct cultivar of Aster plant named 'Thyra Viking', characterized by its rapid growth rate and moderate vigor; freely branching and uniform plant habit; freely flowering even under winter conditions; large daisy-type inflorescences with dark red purple ray florets anf yellow centers; and good post-production longevity.

1 Drawing Sheet

The present invention relates to a new and distinct cultivar of pot Aster plant, botanically known as *Aster novi-belgii* and referred to by the cultivar name Thyra Viking.

The new cultivar is a product of a planned breeding program conducted by the inventor in Årslev, Denmark. The objective of the breeding program was to create new Aster cultivars having desirable inflorescence colors, uniform plant habit and rapid growth rate.

The new cultivar originated from a cross made in 1994, by the inventor of the cultivar Purple Viking (U.S. Plant Patent application filed concurrently) as the male or pollen parent with the cultivar Royal Ruby (not patented) as the female or seed parent.

The cultivar Thyra Viking was discovered and selected by the inventor as a flowering plant within the progeny of the stated cross in a controlled environment in Årslev, Denmark. Asexual reproduction of the new cultivar by terminal cuttings taken at Årslev, Denmark, has shown that the unique features of this Aster are stable and reproduced true to type in successive generations of asexual reproduction.

The following traits have been repeatedly observed and are determined to be the unique characteristics of 'Thyra Viking'. These characteristics in combination distinguish 'Thyra Viking' as a new and distinct cultivar:

1. Rapid growth rate and moderate vigor.
2. Freely branching and uniform plant habit.
3. Freely flowering even under winter conditions.
4. Large daisy-type inflorescences with dark red purple ray florets and yellow centers.
5. Good post-production longevity.

The cultivar Thyra Viking has not been observed under all possible environmental conditions. The phenotype may vary somewhat with variations in environment such as temperature, daylength and light intensity, without, however, any variance in genotype.

In comparison to plants of the new Aster, plants of the male parent, the cultivar Purple Viking, have larger inflorescences. In comparison to plants of the new Aster, plants of the female parent, the cultivar Royal Ruby, are taller, have smaller flowers, differ in ray floret color and have poor postproduction longevity.

The accompanying colored photographs illustrate the overall appearance of the new cultivar, showing the colors as true as it is reasonably possible to obtain in colored reproductions of this type.

The first photograph comprises a top perspective view of typical flowering plant of the new Aster.

The second photograph comprises a top perspective view of a typical inflorescence of the new Aster. Floret and foliage colors in these photographs may vary from the actual ray and foliage colors due to light reflectance.

In the following description, color references are made to The Royal Horticultural Society Colour Chart except where general terms of ordinary dictionary significance are used. The following observations and measurements describe plants grown in Årslev, Denmark, under glass with average day and night temperatures of 20C. Plants received long day/short night treatments for the first six weeks, then short day/long night until flowering. Measurements and numerical values represent ranges or averages for six typical flowering plants.

Botanical classification: *Aster novi-belgii* cultivar Thyra Viking.

Commercial classification: Pot Aster.

Parentage:

*Male or pollen parent.*—*Aster novi-belgii* Purple Viking (U.S. Plant Patent application filed concurrently).

*Female or seed parent.*—*Aster novi-belgii* Royal Ruby (not patented).

Propagation:

*Type.*—Terminal tip cuttings.

*Time to rooting.*—Summer: About 12 days at a temperature of 21C. Winter: About 13 days at a temperature of 21C.

*Rooting habit.*—Fine, fibrous and well-branched.

Plant description:

*Appearance.*—Perennial herbaceous decorative container plant. Stems upright to outward, inverted triangle, uniform habit and very freely branching. Rapid growth rate and moderate vigor. Appropriate for 10 to 15-cm containers. Usually about 11 weeks are required to produce a flowering plant.

*Plant height:* 12 to 15 cm.

*Plant width:* 23 to 27 cm.

*Stem diameter:* 2 to 5 mm.

*Foliage description.*—Arrangement: Distichous. Shape: Elliptic with acute apex and auriculate base, margin entire. Size: Length: 3.5 to 5 cm. Width: 6 to 11 mm. Texture: Glabrous, leathery. Color: Abaxial surface: 137A. Adaxial surface: 137C.

Flowering description:

*Appearance.*—Daisy inflorescence borne on terminals above foliage, arising from leaf axils. Disc and ray florets arranged acropetally on a capitulum.

*Flowering response.*—Under natural conditions, plant flower in the late summer/autumn in the Northern Hemisphere. At other times of the year, inflorescence initiation and development can be induced under short day/long night conditions.

*Post-production longevity.*—Good, inflorescences last about three to four weeks on the plant. Inflorescences persistent.

*Quality of inflorescences.*—Inflorescences form at every leaf axil. Moderate flowering, usually 5 to 8 inflorescences per flowering stem.

*Inflorescence size.*—Diameter: 3 to 3.5 cm. Depth (height): 1 to 1.5 cm. Diameter of disc: 5 to 9 mm.

*Bud.*—Shape: Ovoid. Size: Length: 8 to 10 mm. Diameter: 6 to 8 mm.

*Ray florets.*—Quantity: 100 to 150 per inflorescence. Number of whorls: More than two. Shape: Narrowly obovate with obtuse apex and entire margin. Size: Length: 1.6 to 1.9 cm. Width: 1 to 2 mm. Texture: Satiny, smooth and glabrous. Aspect: Flat to slightly concave. Orientation: Horizontal to peduncle. Color: Mature, abaxial surface: 80A to darker than 80A. Mature, adaxial surface: 82B.

*Disc florets.*—Quantity: 40 to 50 per inflorescence. Length: 6 to 8 mm. Color, apex of corolla; Immature: Dark purple. Mature: Almost transparent.

*Peduncle.*—Aspect: Angled about 45° to the stem. Length: 2.5 to 3 cm. Texture: Glabrous. Color: 137A.

*Reproductive organs.*—Androecium: Present on disc florets only. Anther position: Slightly above the apex of disc corolla. Anther size: 1 to 2 mm. Anther color: 14A. Pollen: Moderate, 14A in color. Gynoecium: Present on both ray and disc florets. Stigma position: Even with the anthers. Stigna shape: Bifurcate. Stigma color: 71A.

Disease resistance: No known Aster diseases observed to date on plants grown under commercial greenhouse conditions.

Seed production: Seed production has not been observed.

It is claimed:

1. A new and distinct cultivar of Aster plant named 'Thyra Viking', as illustrated and described.

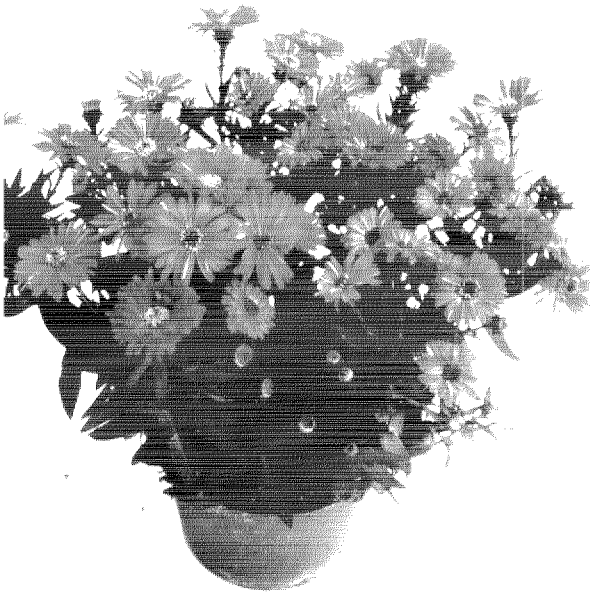
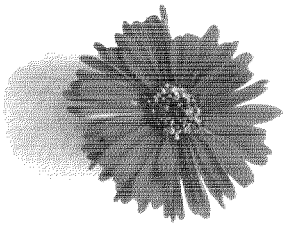

* * * * *